United States Patent
Frank

(10) Patent No.: US 9,638,482 B2
(45) Date of Patent: May 2, 2017

(54) DIGITAL DETECTOR

(71) Applicant: TEXAS INSTRUMENTS DEUTSCHLAND GmbH, Freising (DE)

(72) Inventor: Ingolf E. Frank, Freising (DE)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 430 days.

(21) Appl. No.: 14/141,621

(22) Filed: Dec. 27, 2013

(65) Prior Publication Data

US 2014/0346325 A1   Nov. 27, 2014

(51) Int. Cl.
| | | |
|---|---|---|
| *F41A 3/72* | (2006.01) | |
| *F41A 35/06* | (2006.01) | |
| *G01N 15/06* | (2006.01) | |
| *G01N 21/84* | (2006.01) | |

(52) U.S. Cl.
CPC .............. *F41A 3/72* (2013.01); *F41A 35/06* (2013.01); *G01N 15/06* (2013.01); *G01N 21/84* (2013.01)

(58) Field of Classification Search
CPC ......... G01N 2015/0846; G01N 21/783; G01N 15/06; F41A 35/06
USPC ................ 250/221, 214 A, 214 LA, 214 LS; 340/628, 630
See application file for complete search history.

(56) References Cited

U.S. PATENT DOCUMENTS

| | | | |
|---|---|---|---|
| 3,585,621 A | | 6/1971 | DiCello |
| 4,206,366 A | | 6/1980 | Marsocci et al. |
| 4,300,133 A | | 11/1981 | Solomon |
| 5,705,988 A | * | 1/1998 | McMaster ............ G08B 29/185 340/530 |
| 8,629,779 B2 | * | 1/2014 | Aebersold ............ G08B 17/107 340/628 |
| 2010/0302545 A1 | | 12/2010 | Kajino |
| 2010/0328085 A1 | | 12/2010 | Bohanon |

\* cited by examiner

*Primary Examiner* — Francis M Legasse, Jr.
*Assistant Examiner* — Don Williams
(74) *Attorney, Agent, or Firm* — Gregory J. Albin; Charles A. Brill; Frank D. Cimino

(57) ABSTRACT

The present disclosure provides a digital detector apparatus for use with a sensor unit is provided wherein the sensor unit includes an emitter device and a receiver device, the receiver device having a capacitance. The digital detector apparatus comprises at least a first input port, first output port, and a second output port; and an A/D converter circuit wherein an input of the A/D converter circuit is coupled to the first input port for receiving an output of the receiver device; wherein the first output port of the digital detector apparatus is coupled for charging and discharging the capacitance of the receiver device; the second output port of the digital detector apparatus is coupled for driving the emitter device; and the A/D converter circuit derives a sensor output value from the output of the receiver device during a number of charging and discharging cycles. A digital smoke detector and a method of generating an output signal in a digital detector are also provided.

17 Claims, 11 Drawing Sheets

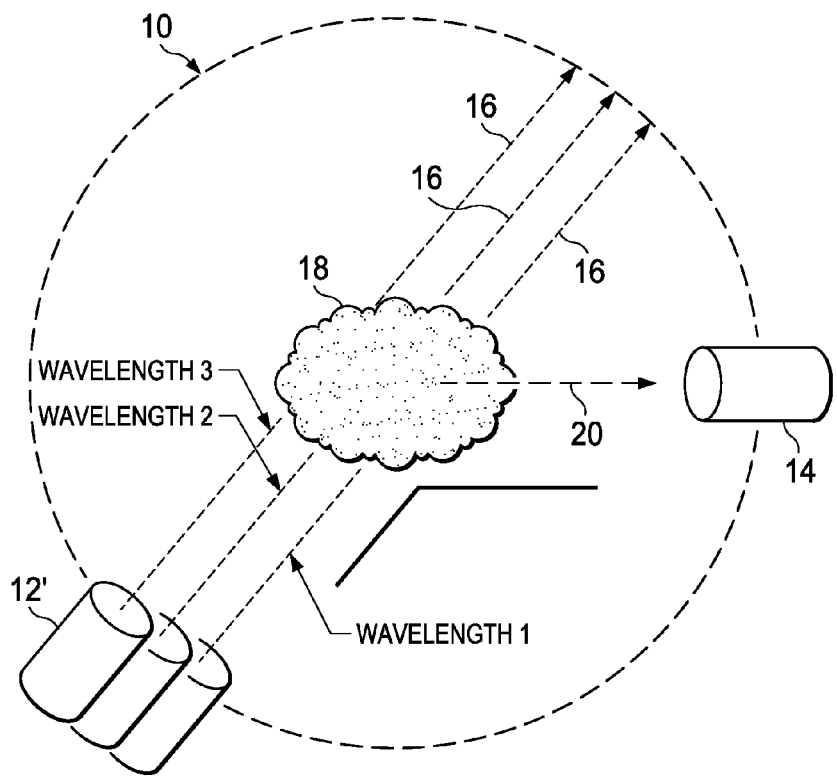
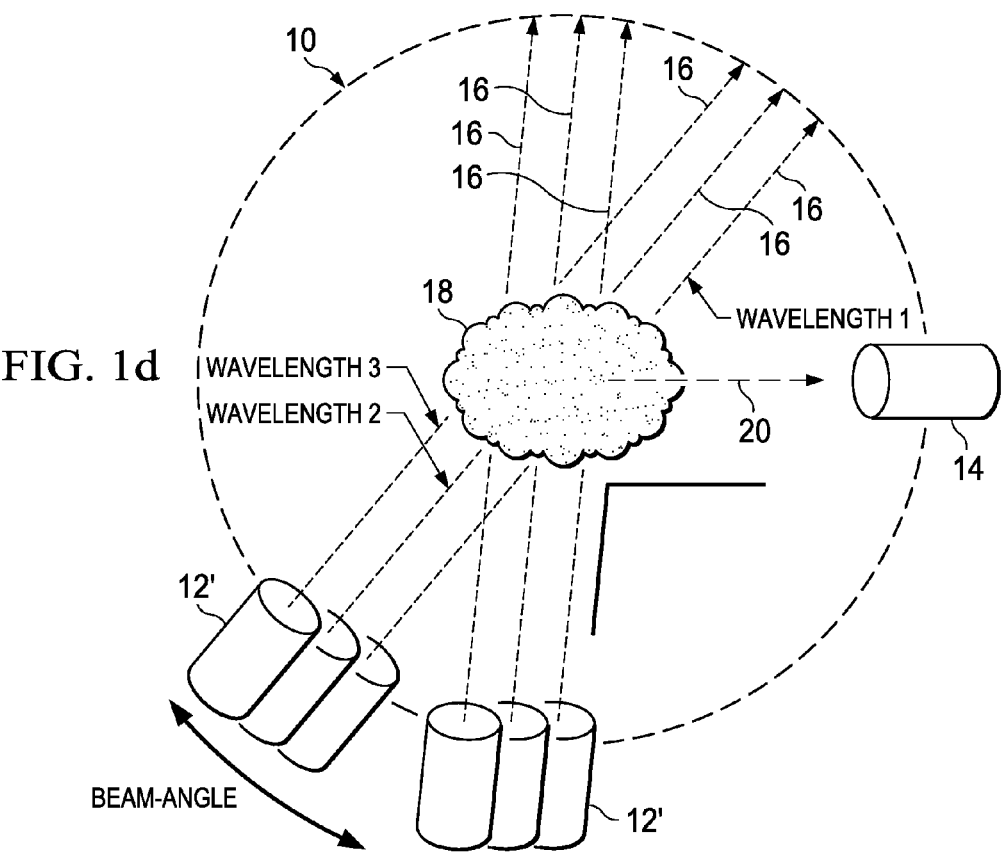

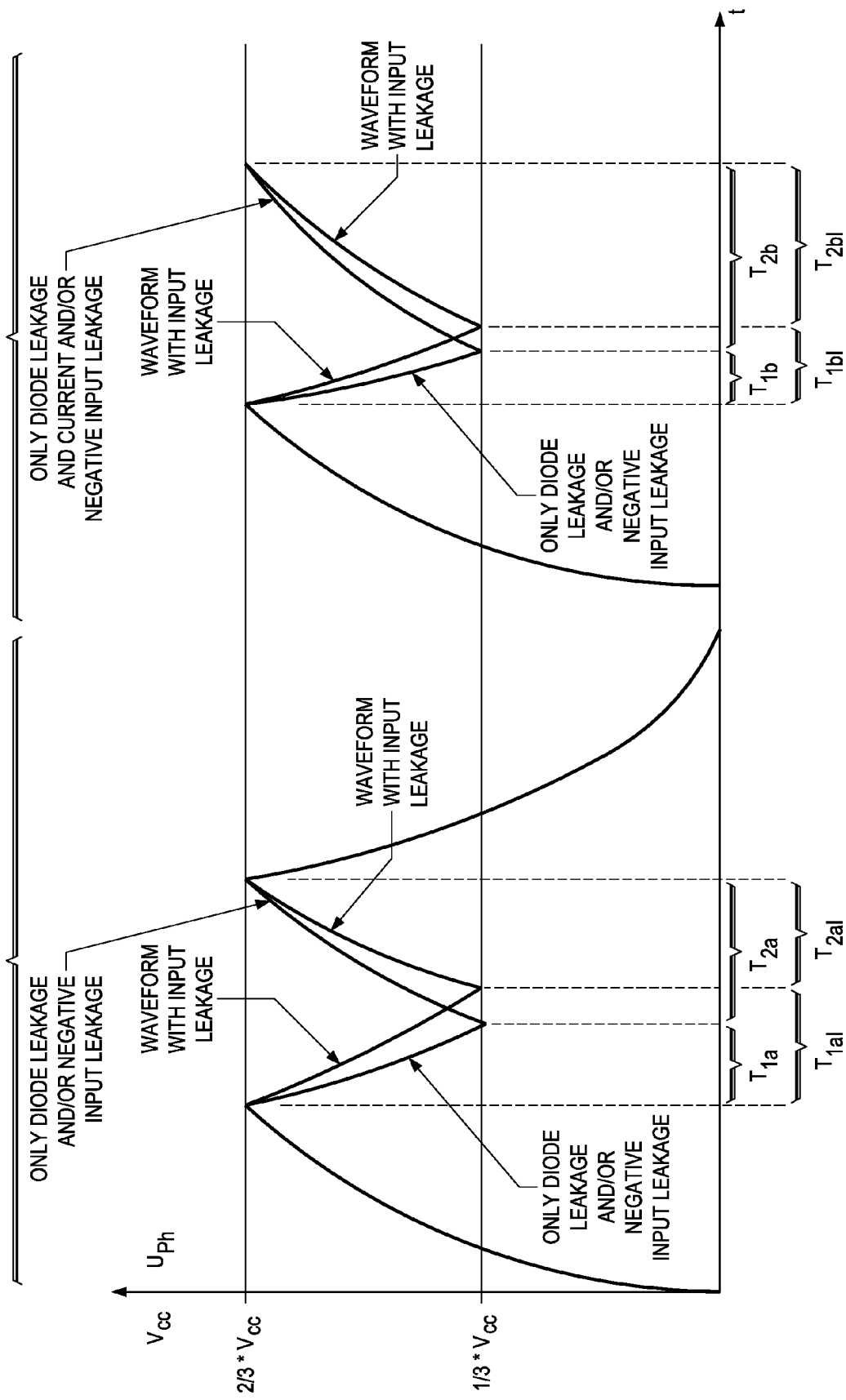

DIGITAL DETECTOR

This application claims the benefit of a U.S. Provisional Application No. 61/826,353, filed May 22, 2013, the entirety of which is hereby incorporated by reference.

FIELD

This application relates to a digital detector apparatus for use with a sensor unit and to a method of generating an output signal in a digital detector. One example of a digital detector apparatus is a photoelectronic smoke detector including a light emitter and a light receiver wherein the invention is not limited to this example but can be used in combination with many sensor units having an emitter and a receiver.

BACKGROUND

Optical smoke detectors, also designated as photoelectric smoke detectors, are known to have a detection chamber in which a light source and a light receiver are located. The interior of the smoke chamber usually is protected from ambient light but includes smoke ports which feed into the dark smoke chamber via a labyrinth of smoke entrances. The light source and the light detector are arranged in the smoke chamber relative to each other in such a way that light emitted from the light source does not directly impinge on the light detector. Rather, the light detector will sense stray light reflected from smoke inside the smoke chamber and hence will generate different output values dependent on the presence or absence of smoke in the chamber. Examples of light sources are light emitting diodes, such as an IR diode or different color diodes. Examples of the light receivers are a photo detector diode and a phototransistor.

The evaluation of the output signal of the photo detector usually requires several analog circuits or specialized integrated circuits which, among others, are needed to improve the signal-noise-ratio (SNR), eliminate adverse effects from the inherent capacitance of the photo diode or other receiver and to amplify the rather weak signal emitted from the photo diodes when exposed to only weak light emittance. One reason why the light emitter will have only a relatively low luminous emittance is that smoke detectors are often used as stand-alone devices, powered by batteries, and need to be able to operate at very low power consumption so as to ensure a long service life.

The output signals of the photo detector hence are typically processed by using a trans-impedance amplifier where the output voltage of the photo detector is stabilized to a fixed voltage level by compensating the discharge current in the detector during light exposure with a charge current from an operational amplifier. By using the trans-impedance amplifier, the voltage at the light receiver is kept constant so that its inherent capacitance does not have to be charged and discharged during detection cycles. This helps to achieve high sensitivity and fast response times. This type of compensating circuit, however, needs a rather large amount of analog discrete components or requires the development of dedicated integrated circuits, hence increasing manufacturing costs for smoke detectors.

In order to improve the sensitivity of smoke detectors, it is known to modulate the light emitted from the light source and demodulate the output signal of the light receiver correspondingly. These modulation techniques are particularly helpful to differentiate within a smoke detection chamber between ambient light and energy from the light source.

Prior art smoke detectors are described in U.S. Pat. No. 4,206,366 A; U.S. Pat. No. 3,585,621 A; U.S. Pat. No. 4,300,133 A; US 2010/0328085 A1; and US 2010/0302545 A1, for example.

SUMMARY

In one example of this disclosure, a digital detector apparatus for use with a sensor unit is provided wherein the sensor unit includes an emitter device and a receiver device, the receiver device having a capacitance. In one or more embodiments, the digital detector apparatus comprises at least a first input port, first output port, and a second output port; and an A/D converter circuit wherein an input of the A/D converter circuit is coupled to the first input port for receiving an output of the receiver device; wherein the first output port of the digital detector apparatus is coupled for charging and discharging the capacitance of the receiver device; the second output port of the digital detector apparatus is coupled for driving the emitter device; and the A/D converter circuit derives a sensor output value from the output of the receiver device during a number of charging and discharging cycles.

The present disclosure also provides a digital smoke detector, including an optical smoke sensor device comprising a light emitter and a light receiver, the light receiver a having capacitance. In one example, the digital smoke detector further includes an integrated circuit device comprising a comparator circuit and a timer, at least a first input port, a first output port and a second output port, wherein an input of the comparator circuit is coupled to the first input port for receiving an voltage across the light receiver; the first output port is coupled to the light receiver for charging and discharging the capacitance of the light receiver; the second output port is coupled to the light emitter for driving the light emitter; and the comparator circuit in combination with the capacitance of the light receiver is part of an A/D converter for deriving a sensor output value.

The present disclosure also provides a method of generating an output signal in a digital detector, the detector comprising an emitter and a receiver, the receiver having a capacitance, and a processing device having at least a first input port, a first output port and a second output port, wherein the first input port is coupled to the receiver for receiving an voltage across the receiver, the first output port is coupled to the receiver for charging and discharging the capacitance of the receiver, and the second output port is coupled to the emitter for driving the emitter. In one example, the method comprises: performing a sequence of charging and discharging cycles of the capacitance of the receiver; during said charging and discharging cycles, selectively driving the emitter; measuring discharging times of the receiver during said charging and discharging cycles; and deriving an alarm signal from measured discharging times.

The present disclosure makes use of the inherent capacitance effect of the receiver of a sensor for implementing an A/D converter circuit with only very few additional passive components and a widely used microcontroller. Charging and discharging of the capacitance of the receiver of the sensor unit is used for deriving a sensor output value at very low power consumption. When applied to a photoelectric smoke detector, it is possible to detect smoke at even weak light conditions using standard photo detector diodes or transistors and a very simply circuit design including a basic general-purpose microcontroller having low power consumption.

While the present disclosure is not limited to a smoke detector or to a detector apparatus for use with a smoke sensor, the principles of this disclosure will be described with reference to a photoelectric smoke detector in the following examples. The person of average skill in the art will understand that these principles can be applied to other types of sensors.

While the invention is defined in the appended claims with reference to a particular combination of features, the person of average skill in the art will also understand that it is within the scope of this disclosure to provide different and additional combinations of features as those explicitly claimed and described.

BRIEF DESCRIPTION OF DRAWINGS

FIG. 1c schematically shows an example of a multi-wave length light beam photoelectric smoke sensor unit according to yet another alternative;

FIG. 1d schematically shows an example of a multi-angle and multi-wavelength light beam photoelectric smoke sensor unit according to another alternative;

FIGS. 10a, 10b, and 11 show examples of output voltages generated by a sensor unit used in the detector circuit of FIG. 8;

DETAILED DESCRIPTION

Figure 1A:
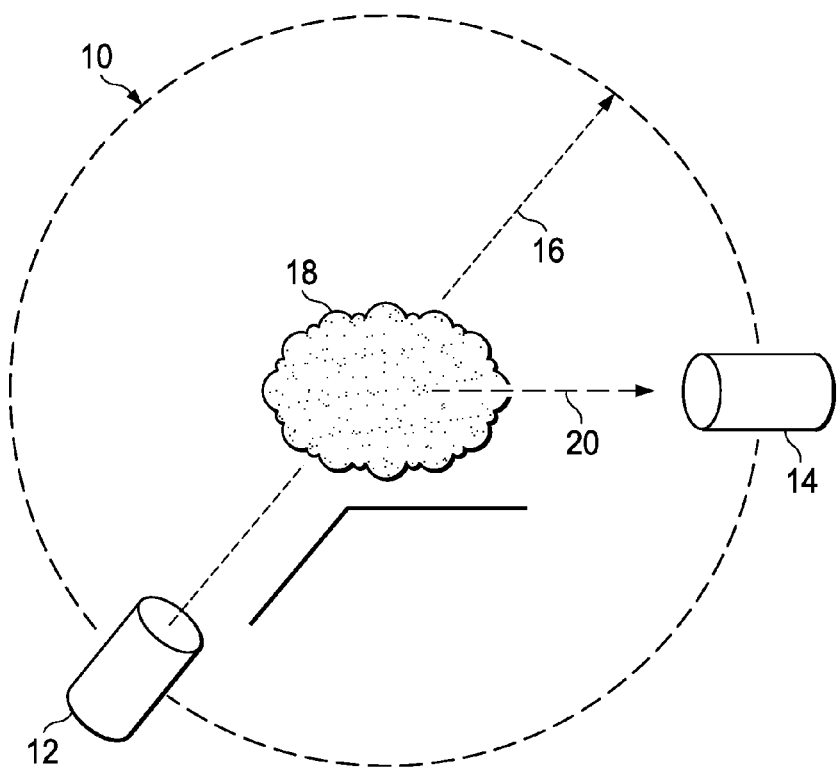
FIG. 1a schematically shows an example of a photoelectric smoke sensor unit.

FIG. 1a schematically shows a photoelectric smoke sensor which can be used as a sensor unit in the present disclosure. The smoke sensor comprises a smoke chamber 10 in which a light emitter 12 and a light receiver 14 are located. The light emitter 12 can be a light emitting diode, such as an IR LED or another color LED, or a white LED and the light receiver can be a photo detector diode or phototransistor or another type of light receiver which has a capacitance.

The light emitter 12 and the light receiver 14 are arranged within the smoke chamber 10 in such a way that direct light 16 emitted from the light emitter 12 does not impinge on the light receiver 14. The smoke chamber 10 also includes smoke ports (not shown) through which smoke can enter into the smoke chamber 10 while preventing the entry of ambient light. Ambient light can be blocked e.g. by providing labyrinth channels (not shown) through which smoke but no light may enter. If smoke 18 is present within the smoke chamber 10, light emitted from the light emitter 12 will be reflected and reflected light 20 will impinge on the light receiver 14.

Figure 1B:
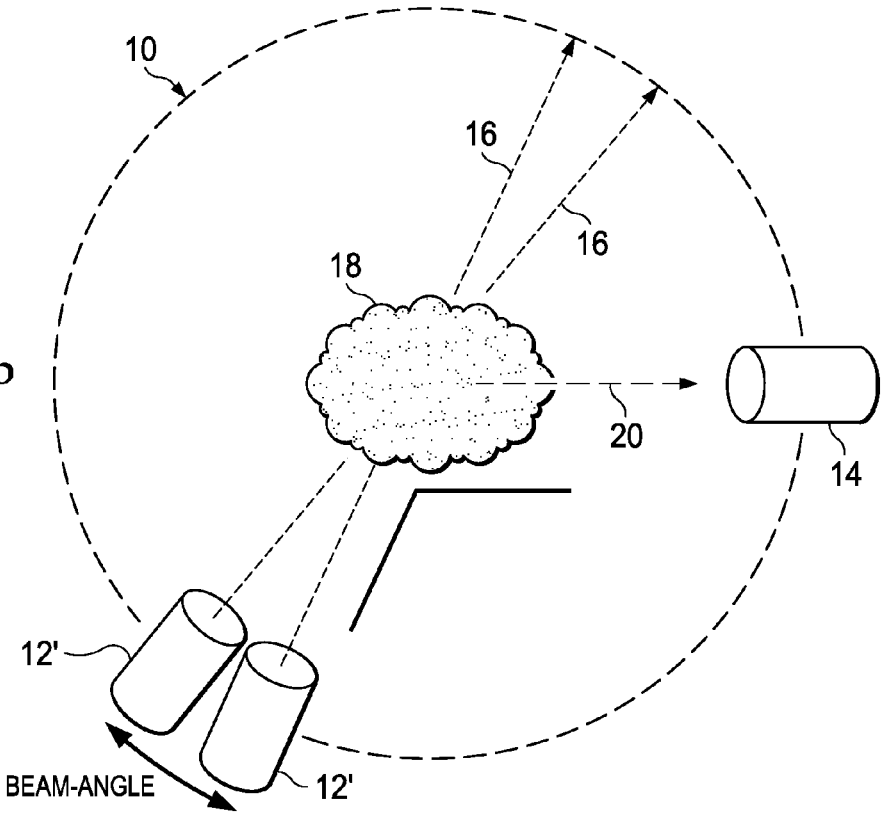
FIG. 1b schematically shows an example of a multi-angle light beam photoelectric smoke sensor unit according to an alternative.

The light receiver 14, such as a photo detector diode, generates an output signal, e.g. an output current or output voltage, which is dependent on the received amount of light but which will also be influenced by other factors, such as the inherent capacitance of the photo diode and previous charging or discharging operations. Moreover, in many applications, such as in smoke detectors and other stand-alone sensor devices, the light emitter can ensure only a rather weak light signal due to power constraints. In particular, in sensor units which have no access to mains but which are supplied via batteries, the sensor unit needs to operate at minimum power consumption so as to guarantee a long service time. For current smoke detectors, for example, it is mandatory that they maintain operation for a duration of ten years or more without servicing and without battery replacement. Alternative smoke detector configurations are shown in FIG. 1b to 1d and will be addressed below.

Figure 2:
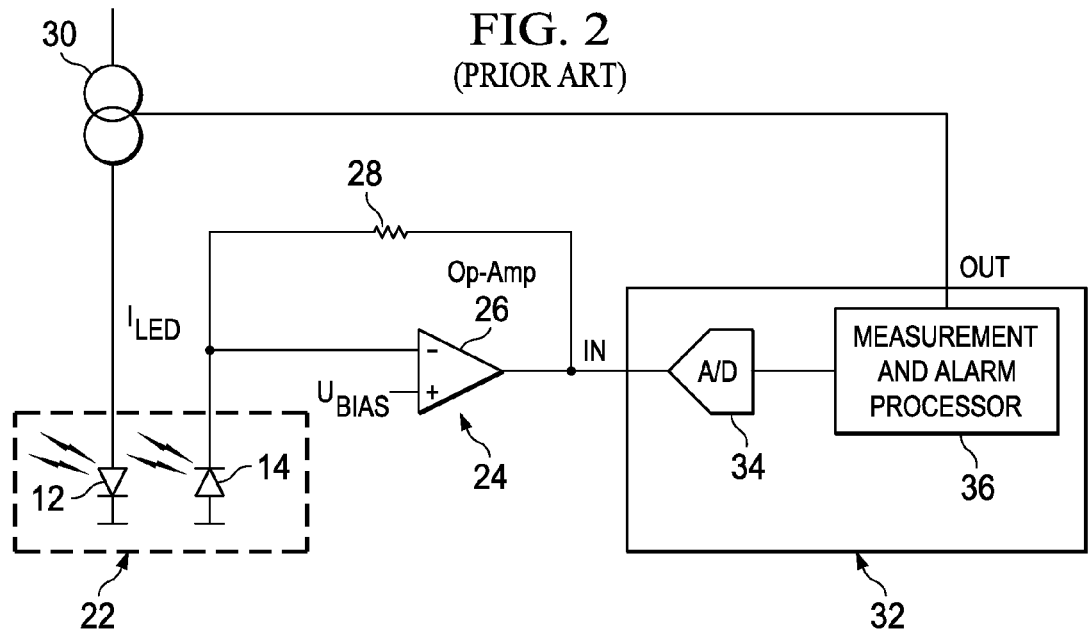
FIG. 2 shows one example of a detector circuit for illustrating the basic operation of the prior art devices.

To meet these demands, it has been known to use amplifier circuits which amplify the weak signal emitted from the photo diodes to improve the SNR and compensate for adverse effects from the inherent capacitance of the photo diode. FIG. 2 schematically shows one example of an amplifier circuit for a photoelectric sensor unit 22 including a light emitter 12 and a light receiver 14. The circuit comprises a trans-impedance amplifier 24, including an operational amplifier 26 and a feedback resistor 28 which are connected to an output node of the sensor unit 22. The trans-impedance amplifier 24 stabilizes the output voltage of the sensor unit 22 to a fixed voltage level by compensating the discharge current which the sensor unit generates during light exposure, with a charge current from the operational amplifier 26. The trans-impedance amplifier 24 thereby also eliminates any effects from a parasitic capacitance of the light receiver 14 which, in the example shown, is a photo diode.

The detector circuit shown in FIG. 2 also comprises a current source 30 for feeding the light emitter 12. In this example, the light emitter is a light emitting diode for producing a light signal which can be detected by the light receiver 14. The circuit further comprises a control unit 32 which can be implemented in a microcontroller, such as Texas Instruments' MSP430™, or in another type of control circuit, including software, hardware and combinations thereof.

The trans-impedance amplifier 24 converts the current change in the light receiver 14 to a voltage change which is input to the control unit 32. The control unit 32 comprises an analog-to-digital (A/D) converter 34 and a measurement and alarm processor 36. The control circuit 32 can drive the current source 30 via an output port OUT so as to drive the light emitter 12. Light emitted from the light emitter 12 charges the light receiver which hence produces a corresponding discharge current. The discharge current is converted into a sensor voltage by the trans-impedance amplifier which is applied to the input port IN of the control circuit. The A/D converter 34 feeds the sensor voltage to the measurement and alarm processor 36 which evaluates a voltage change to determine whether smoke is present in the sensor unit. As explained, the light emitted from the light emitter 12 will be reflected onto the light receiver 14 only when smoke is present in the smoke chamber wherein the photo diode of the light receiver 14 will be charged dependent on whether the light emitter 12 is emitting light or not and, when the light emitter is emitting light, whether there is smoke present in the smoke chamber or not. By evaluating the respective voltage changes in the control circuit 32, the control circuit can detect whether there is smoke present in the sensor unit 22 and generate a corresponding alarm signal.

Figure 3:
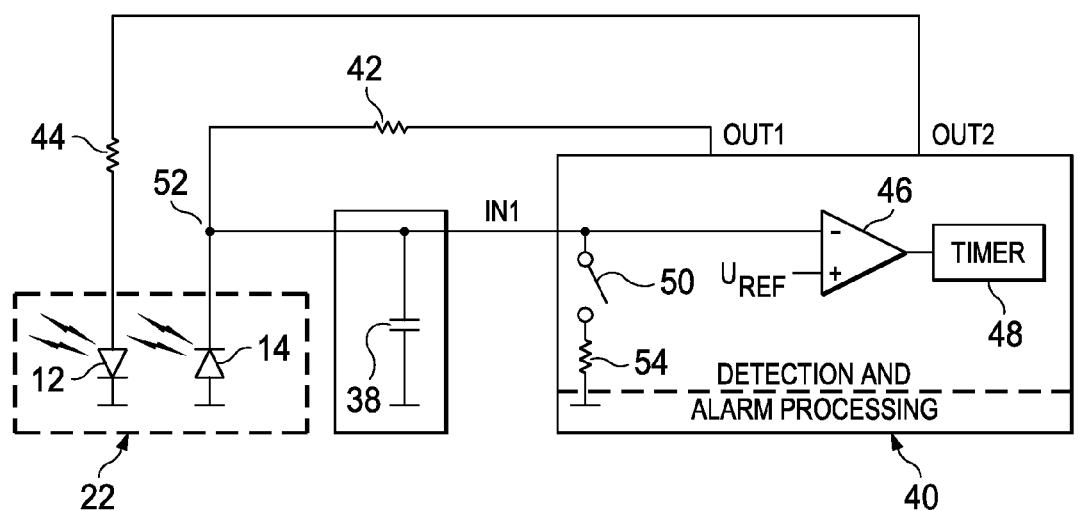
FIG. 3 schematically shows one example of a detector circuit.

FIG. 3 schematically shows a circuit diagram of a digital detector apparatus according to one example. The digital detector apparatus of this and the following examples is described with reference to a photoelectric smoke detector. The person of average skill in the art will under-stand that the detector apparatus can be used in combination with other types of sensor units by applying the principles described herein.

In the example of FIG. 3, the digital detector apparatus is connected to a sensor unit 22 including a light emitter 12 and a light receiver 14 wherein the light emitter 12 will be referred to as a light emitting diode (LED) and the light receiver 14 will be referred to as a photo diode in the following description, without limiting the disclosure thereto.

FIG. 3 shows an optional capacitor which is connected in parallel to the photo diode 14 and may be provided in certain applications to prevent that the input of the comparator 46 goes into saturation due to too high voltage during charging and discharging of the photo diode.

In the example of FIG. 3, the digital detector apparatus comprises a microcontroller 40 and only a minimum amount of passive components, such as first and second resistors 42, 44, for processing the output signal of the sensor unit 22 and for generating an alarm signal. The microcontroller can be one of a great variety of widely-used microcontrollers, such as Texas Instruments' MSP430™. The advantage of using a general-purpose microcontroller is that, besides low costs, microcontrollers which can be used in a large variety of applications are usually optimized in terms of power consumption when compared to dedicated special-purpose microcontrollers. The effort that goes into designing low-power microcontrollers can be high when a microcontroller has high versatility. In one example, the digital detector apparatus hence uses an ultra-low power microcontroller which provides integrated peripherals and can guarantee a battery life of >20 years, having operation characteristics such as <100 µA/MHz; <0.1 µA RAM retention; and <1 µA RTC Mode. However, it should be noted that the invention is not limited to use of any particular type of microcontroller and the functionality of the digital detector apparatus described herein can be implemented by different hardware and/or software arrangements.

In the example described with reference to FIG. 3, the microcontroller 40 comprises a comparator 46, a timer 48 and a switch 50. The microcontroller 40 further comprises one or more software modules (not shown) for processing the signals derived via the comparator 46 and the timer 48 and for generating a control sequence for deriving a detector output signal. While the control functions of the microcontroller can be provided in software, it is also possible to provide a corresponding hardware controller.

The microcontroller 40 comprises at least one input port IN, a first output port OUT1 and a second output port OUT2. The input port IN is connected to an output node 52 of the photo diode 14 and the first output port OUT1 is connected to the same output node 52 via a resistor 42. The second output port OUT2 is connected to the LED 12 via the resistor 44. In general, the LED 12 and the photo diode 14 can be connected to a high voltage or rail voltage, sometimes also designated as "battery voltage", via the output ports OUT1 and OUT2 of the microcontroller 40, these output ports being switched according the control sequence described herein. In the example, OUTx are rail to rail driving outputs so that the battery voltage or other supply voltage is visible at the outputs.

The control sequence of the invention is based on separating the discharge and charge process of the photo diode 14 in time and using the inherent capacitance effect of the photo diode 14 in an analog-to-digital (A/D) converter circuit comprising the comparator 46. The microcontroller 40, via the first output port OUT1, the first input port IN and the switch 50 performs a sequence of a charging and discharging cycles of the photo diode 14. During the charging and discharging cycles, the microcontroller 40 selectively drives the LED 12 via the second output port OUT2. The microcontroller 40, via the comparator 46, digitizes the photo diode output, received at the first input IN, and measures discharging times via the timer 48. The microcontroller 40 derives an output signal from the measured discharging times and further can generate an alarm signal. At least the first output port OUT1 is a tri-state port which can provide a high voltage output, a low voltage output and a high-impedance state.

Figure 4A:
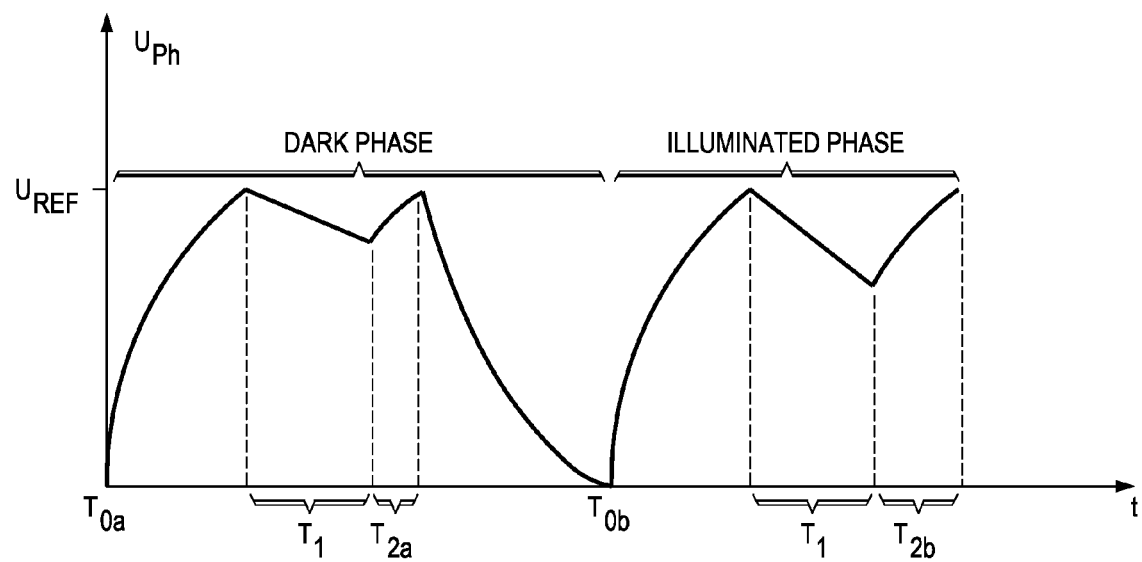
FIGS. 4a and 4b show examples of output voltages generated by a sensor unit used in the detector circuit of FIG. 3, FIG. 5 schematically shows another example of a detector circuit.

One example of operating the photo detector circuit shown in FIG. 3 is now described with reference to FIG. 4a. The control sequence starts with generating a defined initial state by fully or at least essentially discharging the photo diode 14 and then charging the photo diode 14 to a defined reference voltage $U_{REF}$. FIG. 4a shows the output voltage $U_{PH}$ of the photo diode 14, seen at the output node 52, over time (t). The control sequence starts with connecting the first input port IN to a low voltage by closing switch 50 and hence connecting the input port IN to the low voltage rail, such as ground, via impedance 54. The first and second output ports OUT1, OUT2 are at a low voltage, such as ground, and the photo diode 14 hence is discharged via impedance 54. The discharge time is sufficiently long to ensure that the output voltage of photo diode 14, at output node 52 is below some defined level.

Subsequently, the photo diode 14 is charged to a defined level, such as $U_{REF}$, by opening the switch 50 and hence setting the first input port IN to a high-impedance state, and by setting the first output port OUT1 to a high voltage, such as a supply voltage or battery voltage. The state of the second output port OUT2 is unchanged. The output voltage $U_{PH}$ of the photo diode 14 at output node 52 hence starts to increase, as is shown in the first time period preceding $T_1$ in FIG. 4a. The microcontroller 40, via the comparator 46, detects the output voltage $U_{PH}$ of the photo diode 14 and compares said output voltage to the reference voltage $U_{REF}$.

When the output voltage of the photo diode 14 at the output node 52 reaches said reference voltage $U_{REF}$, the comparator 46 starts the timer 48. At the same time, the first output port OUT1 is set to a high-impedance state, while the switch 50 remains open and the second output port OUT2 remains low. The photo diode 14 hence is discharged by a so-called dark current, i.e. a discharge current generated when the photo diode is not illuminated. Discharging of the photo diode 14 continues during a set time period $T_1$.

When said set time period $T_1$ has elapsed, the output voltage of the photo diode 14 should have decreased to some value $<U_{REF}$ due to the dark discharge current. This is shown in FIG. 4a. (In some cases, the output voltage of the photo diode 14 might have increased to a value >$U_{REF}$ due to a leakage current which flows from the microcontroller 40 into the photo diode 14. Such leakage current can occur due to aging of the components. A variant of the control sequence for handling such leakage current is explained further below.)

If the output voltage of the photo diode 14 hence is equal to or smaller than the reference voltage $U_{REF}$, after the set time period $T_1$, the first output port OUT1 is set to the high voltage, e.g. VCC, for charging the capacitance of the photo diode 14 via the resistor 42 while the second output port OUT2 is maintained at the low voltage and the switch 50 is kept open. At the same time, the timer 48 is restarted. The comparator 46 continues to monitor the output voltage of the photo diode 14 at the output node 52 and when the output voltage $U_{PH}$ of the photo diode 14 again reaches the reference voltage $U_{REF}$, a first elapsed time $T_{2A}$, from restarting of the timer, is measured and stored in the microcontroller 40. Then, a first "dark" measurement phase is completed and a second "illuminated" measurement phase is started.

The second "illuminated" measurement phase begins just in the same way as the first "dark" measurement phase by fully or substantially discharging the photo diode 14 so as to generate a defined initial state. As before, the first output port IN is hence connected to the low voltage, e.g. ground, for discharging the capacitance of the photo diode 14, while the first and second output ports OUT1, OUT2 are at the low voltage, e.g. ground. The low voltage at the first input port IN can be generated by closing the switch 50. When the photo diode 14 is discharged for a time which is sufficiently long to ensure an output voltage below some defined level, the first input port IN is set to a high-impedance state, for example by opening the switch 50, and the first output port OUT1 is set to a high voltage, for example VCC, for charging the photo diode 14.

As before, when the output voltage $U_{PH}$ of the photo diode 14 at the output node 52 reaches the reference voltage $U_{REF}$, the first output port OUT1 is set to a high-impedance state, while the switch 50 remains open. This time, however, the second output port OUT2 is set to the high voltage, such as VCC, for activating the LED 12 so that it emits light in the smoke chamber. At the same time, the timer 48 is started.

After the set time period $T_1$, the output voltage of the photo diode 14 should be equal to or smaller than the reference voltage $U_{REF}$, as shown in FIG. 4a (if there is no substantial leakage current, discussed below). At this time, the second output port OUT2 is again set to the low voltage and the first output port OUT1 is set to the high voltage for charging the capacitance of the photo diode 14. At the same time, the timer 48 is restarted. The comparator 46 continues to monitor the output voltage of the photo diode 14.

When the output voltage $U_{PH}$ of the photo diode 14 again reaches the reference voltage $U_{REF}$, a second elapsed time $T_{2B}$ is measured and stored. Because the photo diode 14 is illuminated during the first set time period $T_1$, the discharge current is higher than during the first "dark" measurement phase and the output voltage $U_{PH}$ of the photo diode 14 at the beginning of the second measurement phase $T_{2B}$ is lower than at the beginning of the first measurement phase $T_{2A}$. If there is no smoke present in the smoke chamber, the discharge current in this "illuminated" measurement phase might increase only insignificantly, because the light of the LED 12 does not reach the photo diode 14. If, however, there is smoke in the smoke chamber, the light emitted from the LED 12 is reflected onto the photo diode 14, and the discharge current should be considerably higher during the "illuminated" measurement phase $T_1$. Accordingly, also the second elapsed time $T_{2B}$ will increase accordingly.

The microcontroller 40 hence can derive a sensor output by evaluating the second elapsed time $T_{2B}$ relative to the first elapsed time $T_{2A}$, e.g. by calculating a difference between the second elapsed time $T_{2B}$ and the first elapsed time $T_{2A}$, $T_{2B}$-$T_{2A}$.

When processing the measurement result of the A/D converter, it is possible to adjust the charging/discharging cycles by, for example, providing a first measurement cycle at a first predetermined frequency, such as every 5 seconds, and by increasing said frequency when a certain threshold of the difference between the first and second elapsed times $T_{2B}$-$T_{2A}$, is exceeded. It is also possible to form an average or a moving average over several measurement results and compare said average with a respective threshold.

In another variant, it is also possible to set the threshold very close to a difference of $T_{2B}$-$T_{2A}$ which would be expected when the sensor unit just begins to sense the presence of smoke (or any other parameter to be detected) and to perform a statistical evaluation of exceeded thresholds. The numbers of exceeded thresholds would then be a measure for the presence of smoke (or other parameters to be detected).

It is also possible to perform different and additional types of processing of the signals derived by the comparator 46 and the timer 48 in the microcontroller 40. For example, it is possible to vary the charge and discharge cycles according to different patterns, it is possible to drive the LED 12 using a pulse pattern to reduce energy consumption, it is possible to run through several charging and discharging cycles so as to determine multiple first and second elapse times $T_{2A}$, $T_{2B}$ and process said times by averaging, filtering, integrating, modulating etc. This type of process is performed so as to improve the signal-to-noise ratio (SNR) and to reduce power consumption. Further examples of variants are described below.

Figure 4B:
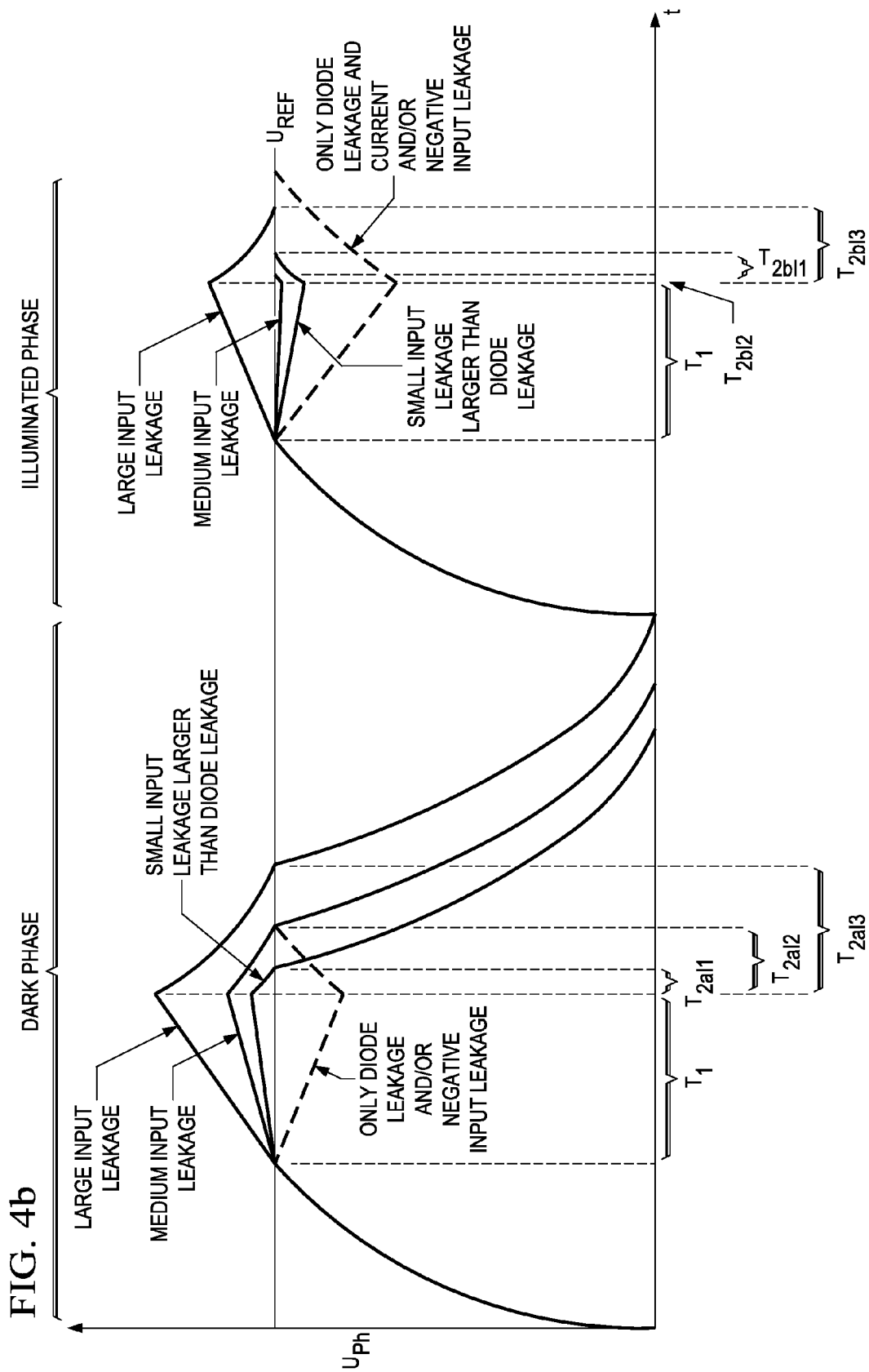

As explained with reference to FIG. 4a, at the end of the first set period $T_1$, the photo diode 14 normally should have been discharged by the dark discharge current or light discharge current (depending on whether the LED 12 was activated during the set period $T_1$). However, if there is a considerable leakage current from the microcontroller 40 which will flow into the photo diode 14 via the input port IN, it can happen that the photo diode 14 is additionally charged during the first set period $T_1$ so that, at the end of the first set period $T_1$, the output voltage $U_{PH}$ of the photo diode 14 is larger than at the beginning of the time period $T_1$, as shown in FIG. 4b.

A variant of the example described with reference to FIG. 4a, is now explained with reference to FIG. 4b: This variant takes into account cases where the photo diode 14 is additionally charged during the first set period $T_1$ by a small, medium or large input leakage current so that, at the end of the first set period $T_1$, the output voltage $U_{PH}$ of the photo diode 14 is larger than at the beginning of the time period $T_1$, as shown in FIG. 4b. Accordingly, at the end of the first set period $T_1$, it is determined whether the output voltage $U_{PH}$ of the photo diode 14 is equal to or smaller than the reference voltage $U_{REF}$ or whether it is larger than the reference voltage $U_{REF}$. If the output $U_{PH}$ is equal to or smaller than the reference voltage $U_{REF}$, the first output port OUT1 is set to the high voltage for recharging the capacitance of the photo diode 14, as described above. If, however, the output voltage $U_{PH}$ of the photo diode 14 is larger than the reference voltage $U_{REF}$, at the end of the set time period $T_1$, the first output port is set to the low voltage for discharging the capacitance of the photo diode 14, while maintaining the second output port OUT2 at the low voltage. The timer 48 is restarted and the detection process proceeds as described above by measuring first and second elapsed times $T_{2A}$, $T_{2B}$, when the output voltage $U_{PH}$ of the photo diode 14 again reaches the reference voltage $U_{FF}$. This modification may happen both in the "dark" measurement phase and the "illuminated" measurement phase. The respective voltage curves are indicated by dashed lines in FIG. 4b. FIG. 4b shows how the elapsed times $T_{2a}$ and $T_{2b}$ may vary according to the level of the leakage current, the three levels being designated by 11, 12, and 13.

As described above, the microcontroller 40 can derive the sensor output value from a difference between the second elapsed time $T_{2B}$ and the first elapsed time $T_{2A}$. If, during the "dark" measurement phase, the output voltage $U_{PH}$ of the photo diode 14, at the end of the set time period $T_1$, was larger than the reference voltage $U_{REF}$, the first elapsed time $T_{2A}$ is inverted to $-T_{2A}$; and if, during the "illuminated" measurement phase, the output voltage $U_{PH}$ of the photo diode 14, at the end of the set time period $T_1$, is larger than the reference voltage $U_{REF}$, the second elapsed time $T_{2B}$ is inverted to $-T_{2B}$ when calculating the difference between $T_{2B}$ and $T_{2A}$, $T_{2B}$-$T_{2A}$. The described example hence provides a processing algorithm in which effects due to leakage current, which flows from the microcontroller 40 or any other components of the photo detector apparatus into the photo diode 14, can be canceled automatically.

Figure 5:
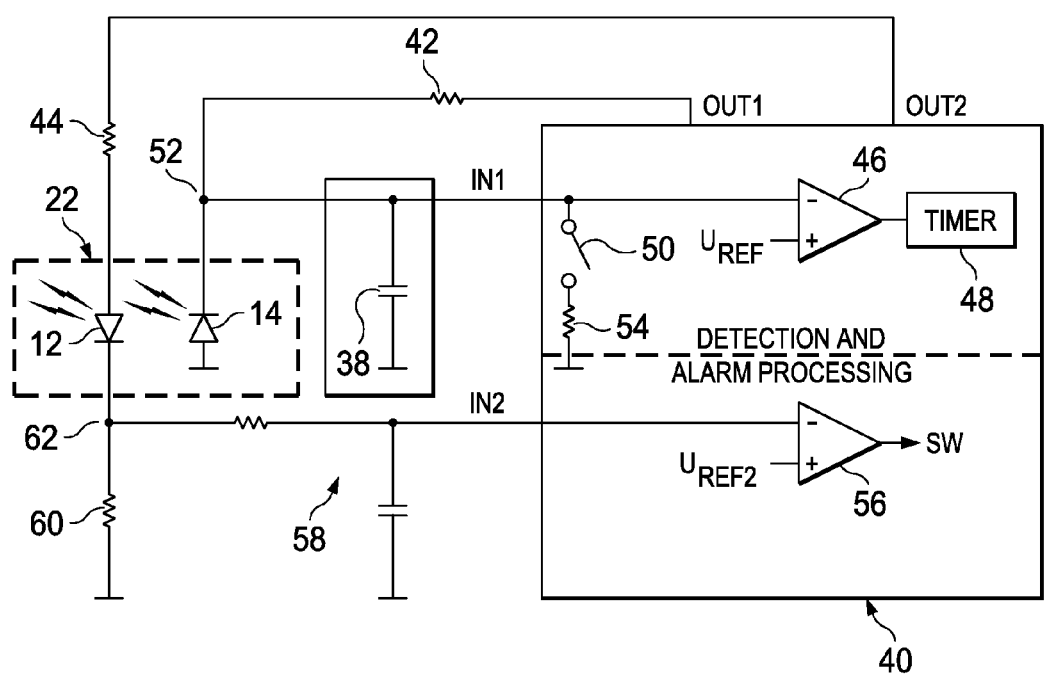

FIG. 5 shows a schematic circuit diagram of a variant of the example described with reference to FIG. 3. Corresponding components are designated by the same reference numbers. These components will not be described again but reference is made to the above description of FIG. 3.

In the variant of FIG. 5, the microcontroller 40 provides an additional comparator 56 which may be an additional comparator device or which can be implemented by the same comparator device as the comparator 46 in combination with a multiplexer (not shown). The comparator 56 is connected to a second input port IN2 and also receives a second reference voltage $U_{REF2}$. Its output is processed by the microcontroller 40 in one or more software modules as described below. The second input port IN2 of the microcontroller 40 is connected to the LED 12 via an R/C component 58, including a resistor and a capacitance at an output node 62. The LED 12 is further connected to a low voltage, such as ground, via a further resistor 60 at the output node 62.

The R/C component 58 in combination with the comparator 56 forms an A/D converter which is used to measure the current flowing through the light emitter 12, such as an IR LED. Its output signal is processed by the microcontroller 40 in order to adjust the illumination time, i.e. the set time period $T_1$ during the "illuminated" measurement phase, so as to emit a defined amount of light energy. Alternatively, the output of the second comparator 56 can be used to proportionally adjust the result of the sensor output calculation $T_{2B}$-$T_{2A}$ or the alarm threshold level as a function of the amount of light actually emitted by the LED 12 if the set time period $T_1$ shall not be changed.

Figure 6:
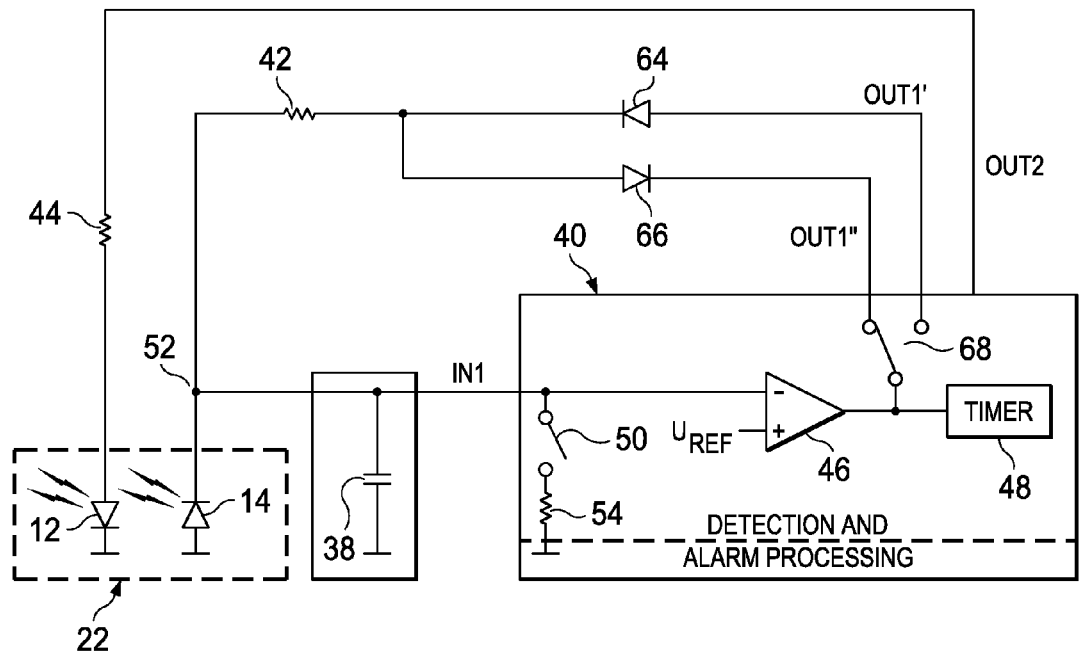
FIG. 6 schematically shows another example of a detector circuit.

FIG. 6 shows a schematic circuit diagram of another example of a digital detector apparatus which is a variant of the circuit of FIG. 3. As far as the circuit of FIG. 6 corresponds to the circuit of FIG. 3, the same or similar components have been designated by the same reference numbers and reference is made to the description of FIG. 3 above. As in the previous examples, the photo detector apparatus comprises a sensor unit 22 including a light emitter 12, such as an LED, and a light receiver 14, such as a photo diode. The output of the photo diode 14 is connected to an output node 52 and an optional capacitor 38 is connected in parallel to the photo diode 14. The output node 52 is connected to an input port IN of a microcontroller 40 and further is connected to a first output port OUT1 of the microcontroller 40 via a first resistor 42. The LED 12 is connected to a second output port OUT2 of the microcontroller 40 via a second resistor 44.

As in the previous example, the microcontroller 40 comprises at least a comparator 46, a timer 48, and a switch 50 wherein the switch 50 is connected to a low voltage, such as ground, via impedance 54. As in the previous example, the microcontroller 40 implements a control circuit which, in the examples described, is provided as an integrated circuit but which also could be provided by any suitable combination of hardware and software, including a hard-wired circuit. In one example, the microcontroller 40 is a mixed-signal processor designed for ultra-low power consumption, which is a general-purpose microcontroller having a mix of integrated peripherals for a variety of applications. One example is an MSP430™ microcontroller of Texas Instruments which is a 16-Bit, RISC-based, mixed-signal processor. As indicated before this is but one example for implementing the microcontroller 40 and any other integrated circuit or combination of hardware and software can be used for detection and alarm processing.

The example of FIG. 6 differs from those described with reference to FIGS. 3 and 5 in that the output of the comparator 46 is connected to the output node 52 via two blocking diodes 64, 66 which are connected in an anti-parallel configuration. More particularly, the output of the comparator 46 can be directed to two output ports OUT1', OUT1", which together form the first output port, via a switch 68. The switch 68 can be software-driven or hardware-driven to selectively connect the output of the comparator 46 to the output node 52 via either one of the first and second blocking diodes 64, 66.

When compared to the examples described with reference to FIGS. 3 and 5, the state of the output port OUT1 can be set automatically by the output of the comparator 46 instead of processing the output of the comparator 46 by software and driving the first output OUT1 accordingly. This provides a more accurate charge to the photo diode 14 and hence increases the overall measurement accuracy. In the example of FIG. 6, the output port OUT1 is split into two first output ports OUT1', OUT1" to be able to handle also those situations where the photo diode 14, instead of being discharged by a dark/light current, is charged by a leakage current.

One example of controlling the sensor unit 22 and processing the signals derived from the sensor unit 22 is as follows: As in the previous example, the processing sequence starts by connecting the first input port IN to a low voltage, such as ground, via the switch 50 and impedance 54, while the first and second output ports OUT1, comprising OUT1' and OUT1" and OUT2 are at a low voltage. The capacitance of the photo diode 14 is hence discharged in order to create a defined initial state. The first input port IN is then set to a high impedance state by opening the switch 50, and the first output port OUT1 is set to a high voltage by closing the switch 68 on OUT1'. The capacitance of the photo diode 14 hence is charged, as shown in FIG. 4, starting from $T_{0a}$.

When the output voltage of the photo diode 14, detected by the comparator 46, reaches the reference voltage $U_{REF}$, the output of the comparator 46 will go low so that the output port OUT1' is at a low voltage state and the current flow is stopped instantly through the blocking diode 64. At the same time, the timer 48 is started for setting the first time period $T_1$. If there is no or insubstantial leakage current, the photo diode 14 will be discharged during the time period $T_1$ by the dark discharge current. A suitable software module in the micro-processor 40 can set the output port OUT1' into high impedance state before the comparator 46 starts sensing the decrease of voltage. This will block any current flowing from the photo diode 14 back to port OUT1' during $T_1$. The timing for setting port OUT1' into high impedance state is not very critical as the blocking diode 64 prevents the initial backflow of current into port OUT1' and the discharge is comparably slow. If there is leakage current at the input port IN, the photo diode 14 will be charged by said leakage current, as indicated in FIG. 4b, wherein the blocking diode 64 still will block said charge current.

At the end of the first time period $T_1$, if the output voltage of the photo diode 14 is equal to or smaller than the reference voltage $U_{REF}$, as detected by the comparator 46, the first output port OUT1 will again be set to the high voltage, by keeping the switch 68 connected to OUT1' and setting the port to low impedance state for recharging the capacitance of the photo diode 14. At this time, the second output port OUT2 is maintained at the low voltage and the timer is restarted.

If, however, the output voltage of the photo diode 14 has increased during the time period $T_1$ due to leakage current and hence becomes larger than the reference voltage $U_{REF}$, the output of the comparator 46 will go low and the switch 68 will be closed on OUT1" to connect said low voltage to the output node 52 of the photo diode 14. The second output port OUT2 is maintained at the low voltage and the timer is restarted. The capacitance of the photo diode 14 then will be discharged via the second blocking diode 66 and the output port OUT1".

The control sequence then proceeds as described with reference to FIG. 3 wherein the comparator 46 detects when the output voltage $U_{PH}$ of the photo diode 14 again reaches the reference voltage $U_{REF}$ and measures the first elapsed time $T_{2A}$. The first "dark" measurement phase hence is completed and the same sequence is repeated for the second "illuminated" measurement phase, with the only difference being that the second output port OUT2 is set to the high voltage for activating the LED 12 during the first time period $T_1$.

The first and second time periods $T_{2A}$ and $T_{2B}$, determined in the microcontroller 40, can be processed as described in the previous examples.

Figure 7:
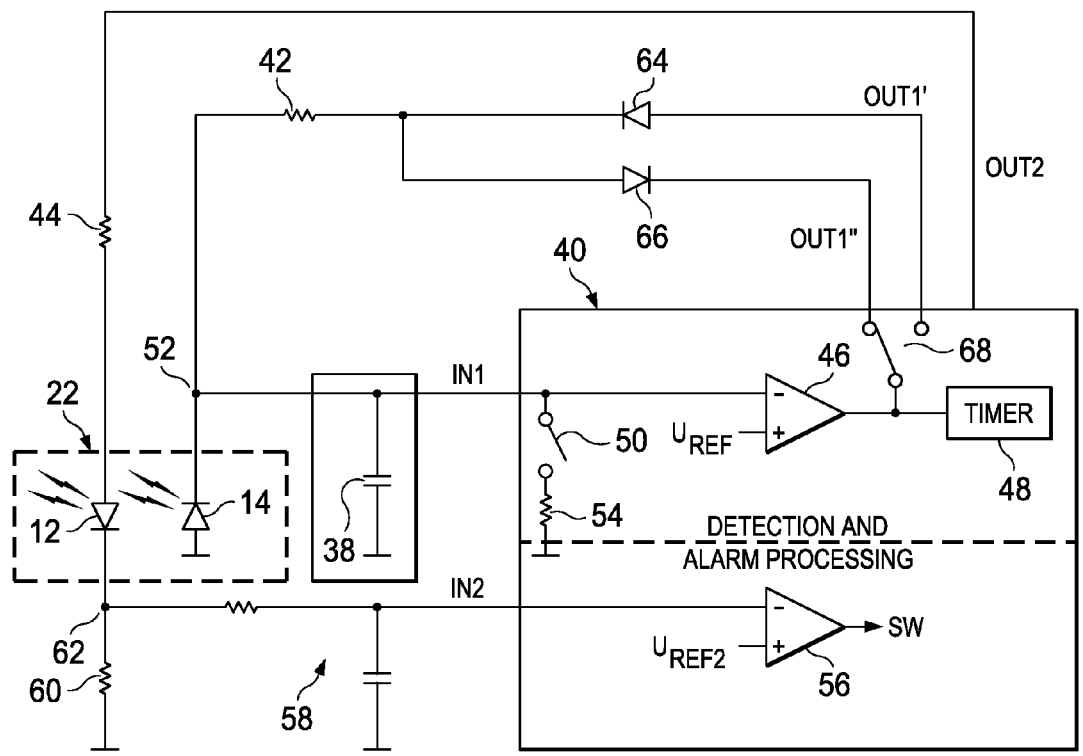
FIG. 7 schematically shows another example of a detector circuit.

FIG. 7 shows a schematic circuit diagram of a variant of the circuit of FIG. 6 including a second comparator 56 for measuring the current flowing through the LED 12 for adjusting either the illumination time during the first time period $T_1$ or for adjusting software threshold levels, such as $U_{REF}$, or both. As in the previous example, comparator 56 can be an additional or the same comparator as comparator 46. In one example, only one comparator in combination with a multiplexer (not shown) can be used to implement both comparator functions. This is possible because the current in the LED 12 and the level compensation on node 52 happen during different times (T1 versus T2). Reference is made to the description of FIG. 5 above.

Figure 8:
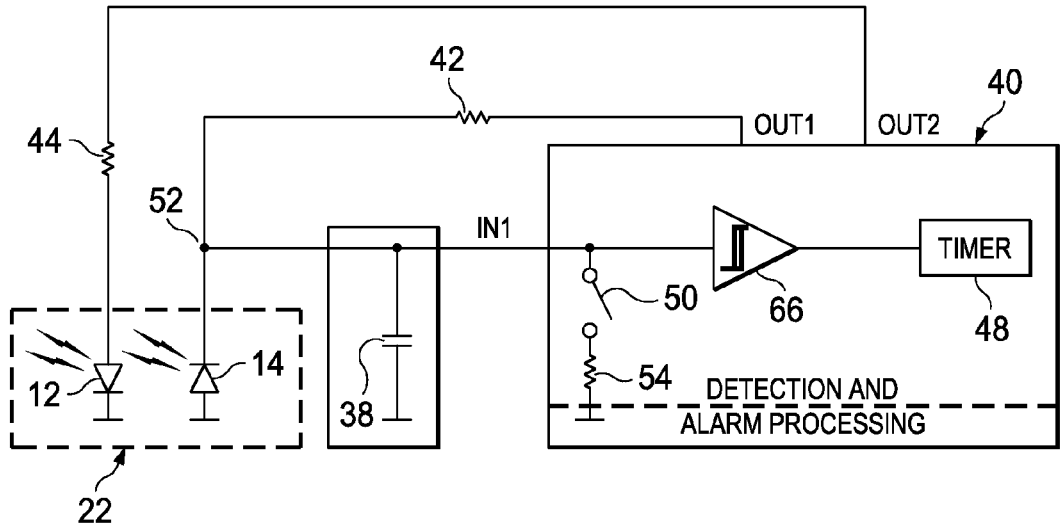
FIG. 8 schematically shows another example of a detector circuit.

FIG. 8 shows a schematic circuit diagram of another example of a digital detector apparatus. As far as the circuit of FIG. 8 corresponds to the circuits of FIGS. 3 and 6, the same or similar components have been designated by the same reference numbers and reference is made to the description of FIGS. 3 and 6 above. As in the previous examples, the photo detector apparatus comprises a sensor unit 22 including a light emitter 12, such as an LED, and a light receiver 14, such as a photo diode. The output of the photo diode 14 is connected to an output node 52 and an optional capacitor 38 is connected in parallel to the photo diode 14. The output node 52 is connected to an input port IN of a microcontroller 40 and further is connected to a first output port OUT1 of the microcontroller 40 via a first resistor 42. The LED 12 is connected to a second output port OUT2 of the microcontroller 40 via a second resistor 44.

As in the previous example, the microcontroller 40 comprises at least a comparator 66, a timer 48, and a switch 50 wherein the switch 50 is connected to a low voltage, such as ground, via impedance 54. As in the previous example, the microcontroller 40 implements a control circuit which, in the examples described, is provided as an integrated circuit but which also could be provided by any suitable combination of hardware and software, including a hard-wired circuit.

The example of FIG. 8 differs from those described with reference to FIGS. 3 and 5 in that the comparator 66 is implemented using a Schmitt trigger circuit; in the following it also will be referred to as Schmitt trigger 66.

One example of controlling the sensor unit 22 and processing the signals derived from the sensor unit 22 using the circuit design of FIG. 8 is described in the following: As in the previous examples, the processing sequence starts by connecting the first input port IN to a low voltage, such as ground, via the switch 50 and impedance 54, while the first and second output ports OUT1 and OUT2 are at a low voltage. The capacitance of the photo diode 14 is hence discharged in order to create a defined initial state.

Figure 10A:
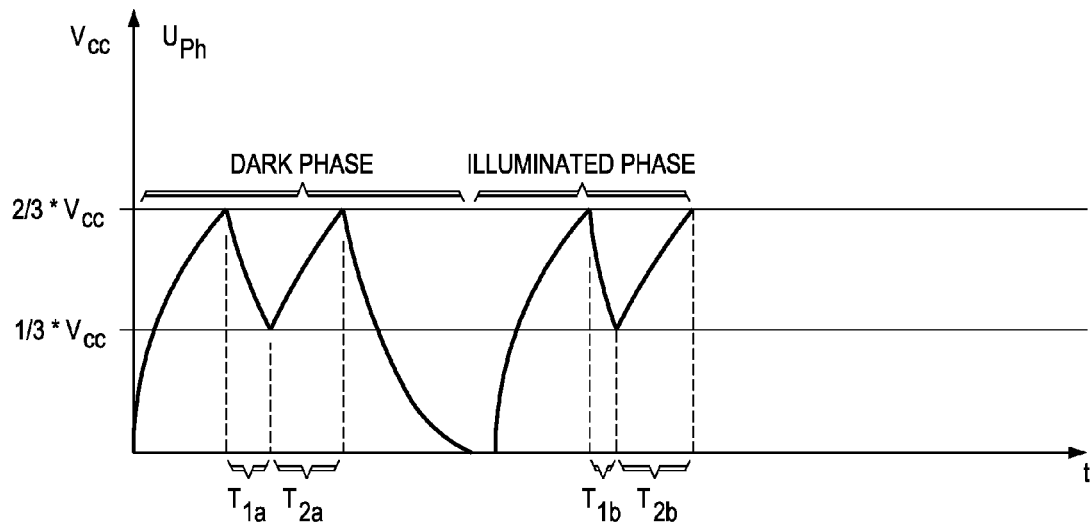

The first input port IN is then set to a high impedance state by opening the switch 50, and the first output port OUT1 is set to a high voltage. The capacitance of the photo diode 14 hence is charged while the second output port OUT2 is at the low voltage, as shown in FIG. 10a at $T_{0a}$.

When the output voltage of the photo diode 14, received at the first input port IN1, reaches an upper trigger level of the Schmitt trigger, the Schmitt trigger 66 will switch to set the first output port OUT1 to the low voltage, for discharging the capacitance of the receiver device. If there is no or insubstantial leakage current, the photo diode 14 will then be discharged by the current flow through resistor 42 until the voltage on IN1 reaches the lower Schmitt trigger threshold. Now OUT1 is set to high impedance leaving the photo diode 14 floating for a time period $T_1$. During this time period, the photo diode 14 is discharged by the dark discharge current. At the end of time period $T_1$, OUT1 is set to the high voltage, charging the photo diode 14 up to the upper Schmitt trigger level, and the timer is started to capture time $T_{2a}$. Once the voltage on IN1 reached the upper trigger level of the Schmitt trigger, time period $T_{2a}$ ends and is captured in the timer 48. The same procedure is repeated with the LED 12 illuminated by setting OUT2 high during $T_1$. If there is smoke present then the resulting higher discharge current in the photo diode 14 leads to a lower voltage at the photo diode than in the dark measurement period due to more rapid discharge. Therefore it takes longer to charge the photo diode 14 to the upper Schmitt trigger level and the recharge time period $T_{2b}$ is longer. The sensor output is calculated from the difference of $T_{2a}$ and $T_{2b}$. If there is leakage current at the input port IN1, as indicated in FIG. 10b, then it affects the photo diode voltage at the end of time period $T_1$ identical in the dark and illuminated measurement. Thus it is cancelling itself out automatically.

The circuit design of FIG. 8 has the advantage of providing a very simple yet efficient solution of a detector apparatus using a Schmitt trigger as comparator. In fact, with the circuit design of FIG. 8, it is even possible to process the output signal of the Schmitt trigger 66 using a simply logic circuit, even without the need of a microcontroller. Leakage currents play no role in this topology as long as the current through resistor 42 is calculated such that the largest possible occurrence of leakage according to the device and system specifications doesn't lead to a voltage change on IN1 opposite to the direction it would have without leakage.

Figure 9:
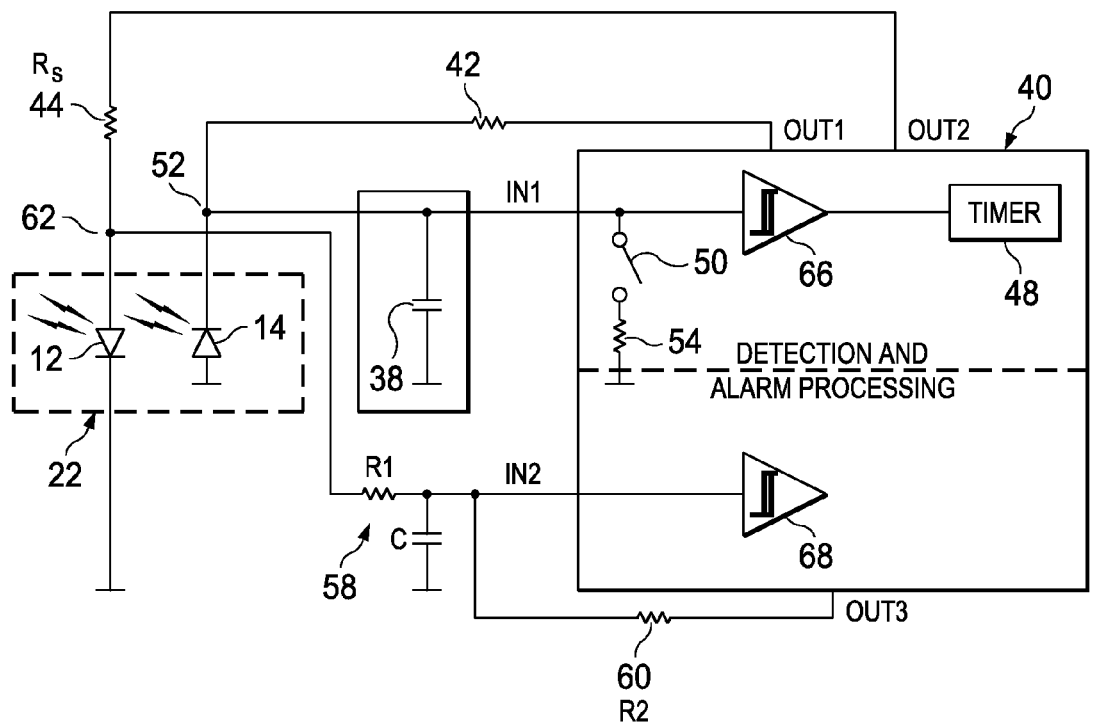
FIG. 9 schematically shows another example of a detector circuit.

FIG. 9 shows a schematic circuit diagram of a variant of the circuit of FIG. 8 including a second Schmitt trigger 68 for measuring the current flowing through the LED 12 for adjusting either the illumination time during the first time period $T_1$ or for adjusting software threshold levels, such as the count threshold at which the alarm is issued, or both. At the beginning of a first measurement, capacitor C is discharged by holding OUT2 and OUT3 low. Then the time $T_a$ is measured, $T_a$ indicating how long it takes to charge the capacitor C up to the upper Schmitt trigger threshold, while OUT2 is still low with the LED 12 dark and OUT3 is high. This measurement can be done in parallel with the previously described dark phase measurement. At the beginning of a second measurement, capacitor C is discharged by holding OUT2 and OUT3 low. Then the time $T_b$ is measured, indicating how long it takes to charge the capacitor C up to the upper Schmitt trigger threshold, while OUT2 is high with the LED 12 illuminated and OUT3 is high. The two measured times $T_a$ and $T_b$ can be used to solve two equations with the two unknown variables 'battery voltage' and 'upper Schmitt trigger threshold voltage'. Based on the battery voltage it is possible to calculate the current flowing through resistor $R_s$ 44 and into the LED 12. The two equations are:

$$U_{threshold} = \frac{U_{battery}}{R_1 + R_2} * R_1 * \left(1 - e^{-\frac{T_a}{RC}}\right)$$

$$U_{threshold} = \left(\frac{U_{battery} - U_d}{R_1 + R_2} * R_1 + U_d\right) * \left(1 - e^{-\frac{T_b}{RC}}\right)$$

For both equations, R is calculated as:

$$R = \frac{R_1 * R_2}{R_1 + R_2}$$

R1, R2 and C are selected such that the upper Schmitt trigger level is always reached and charging of C is finished during the LED illumination time $T_1$ in order to conserve power. $U_d$ is the voltage across LED 12. With $U_d$, $R_1$, $R_2$, C, $T_a$ and $T_b$ known it is possible to calculate $U_{threshold}$ and $U_{battery}$ and finally the current into the LED 12:

$$I_{LED} = \frac{U_{battery} - U_d}{R_s}$$

Based on the LED current $I_{LED}$, either the illumination time during the first time period $T_1$ or the software threshold levels, such as the count threshold at which the alarm is issued, or both can be adjusted.

Figure 13:
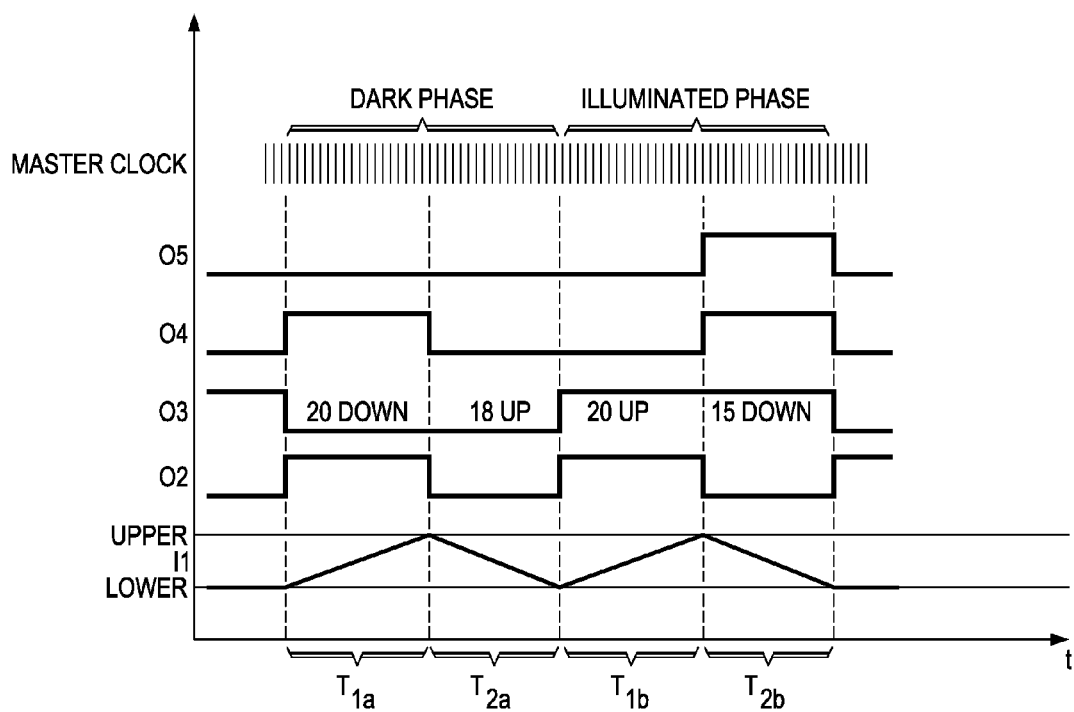
FIG. 13 shows an example of an output voltage generated by a sensor unit used in the detector circuit of FIG. 12.
Figure 11:
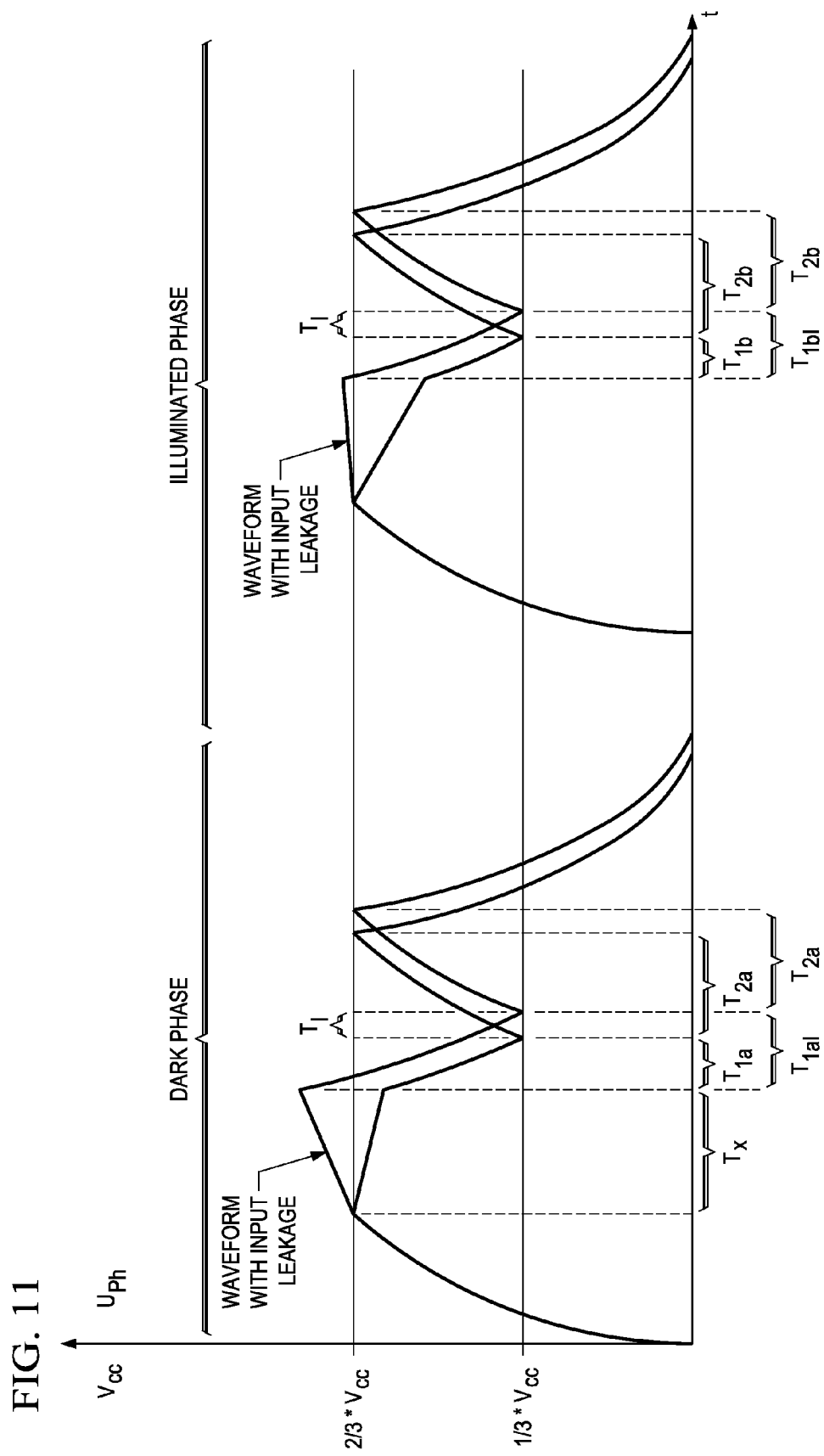

For deriving a detector output, instead of calculating the difference $T_{2B}$-$T_{2A}$, it also is possible to repeat a number of times the sequence of "dark" measurement phase and "illuminated" measurement phase and to calculate the duty cycles of $T_1/T_{2A}$ are as well as the duty cycle of $T_1/T_{2B}$ wherein the detector output corresponds to the ratio of duty cycles. The duty cycles $T_1/T_{2A}$ and $T_1/T_{2B}$ of the Schmitt-trigger 66 will be different whether the photo diode 14 is illuminated or not illuminated during the measurement phase. The change in the duty cycle or even a change in the mean value of duty cycles hence can be used as a measure for the sensor output. The respective processing circuit can be implemented with a small number of discrete components, even without a microcontroller. An example of such circuit is shown in FIG. 12, with the corresponding waveforms in FIG. 13.

Figure 12:
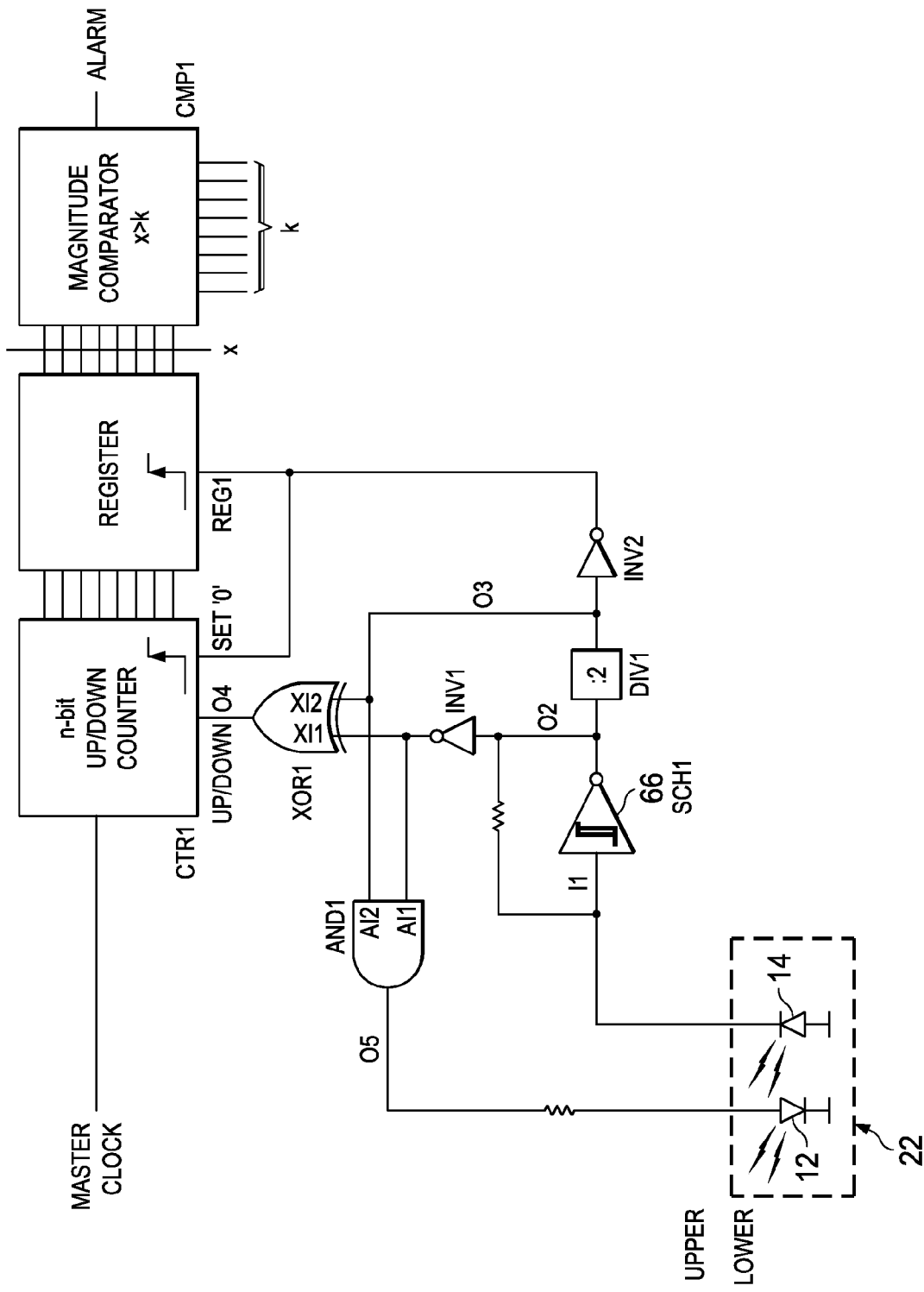
FIG. 12 schematically shows another example of a detector circuit.

In the example of FIG. 12, the Schmitt trigger SCH1, 66, is operating as a low frequency oscillator. The output O2 of the Schmitt trigger SCH1 is connected to a divider DIV1 (in this example, a divider by 2) and to an inverter INV1. The output of the inverter INV1 is connected to an AND gate AND1 and to an X-OR gate XOR1. The output signal O4 from the X-OR gate XOR1 selects between the up or down counting mode of a counter CTR1. The counter CTR1 is continuously counting the clock pulses from a master clock source.

The first measurement cycle starts with charging the photo diode 14 during the dark phase. Output O3 of the divider DIV1 is then low and output O2 of the Schmitt trigger SCH1 is high. The AND gate AND1 has both inputs low. Therefore its output O5 is low as well and the LED 12 is dark. Both inputs of X-OR gate XOR1 are low as well and the output O4 of X-OR gate XOR1 is low. Therefore the counter CTR1 is counting down.

When the photo diode voltage reaches the upper threshold of the Schmitt trigger SCH1, the output O2 of the Schmitt trigger SCH1 turns low and the photo diode 14 starts to discharge. Since divider output O3 is still low the output O5 of the AND gate AND1 is also still low, and the LED 12 remains dark. With one input XI1 of the X-OR gate XOR1 high and the other input XI2 low, the output of the X-OR gate XOR1 turns high and the counter CTR1 starts counting up. Once the photo diode voltage reaches the lower threshold of the Schmitt trigger SCH1, its output O2 switches high and the output O3 of the divider DIV1 also switches high.

Now the first input AI1 of AND gate AND1 is low and the second input AI2 is high so that the output O5 of AND gate AND1 is still low and the LED 12 is still dark. The first input XI1 of the X-OR gate XOR1 is low and the second input XI2 is high so that the output O4 of the X-OR gate XOR1 is high and the counter CTR1 continues counting up. Once the photo diode voltage reaches the upper threshold of the Schmitt trigger SCH1, the output O2 of the Schmitt trigger SCH1 turns low. The first input AI1 and the second input AI2 of the AND gate AND1 are now both high, the output O5 of the AND gate AND1 turns high and the LED 12 is illuminated. Both inputs XI1 and XI2 of the X-OR gate XOR1 are also high so that the output O4 of the X-OR gate XOR1 turns low and the counter CTR1 starts counting down.

Once the photo diode voltage reaches the lower threshold of the Schmitt trigger SCH1 the output O3 of the divider DIV1 goes low and the output of the inverter INV2 goes high. This triggers the register REG1 through its rising edge sensitive trigger input to capture the final count value. It also sets the counter CTR1 back to zero through its rising edge sensitive set to '0' input.

If there was no smoke present, then the photo diode 14 would receive no light and was only discharged by the Schmitt trigger SCH1. In this case, the count time for discharging the photo diode 14 is the same as during the dark phase and the down-count value is matching the up-count value during discharge in the dark phase. The final count value of the counter CTR1 will therefore be close to zero. If there was smoke present, then the photo diode 14 would receive light and the discharge of the photo diode 14 went faster. Thus the down-count value is smaller. Therefore the final counter value is then greater than zero and potentially indicates an alarm condition if the count value 'x' is even greater than a threshold value 'k'.

A magnitude comparator CMP1 tests for this condition and sets its output 'Alarm' accordingly. Since the up-count and down-count directions for counter CTR1 are complementary for the dark and the illuminated measurement phases, any duty cycle distortions are compensated to zero. The light resulting from smoke is affecting only the discharge phase of the illuminated measurement phase by shortening this phase and therefore affects the balance of the up-count and down-count values resulting in a positive counter value.

The capacity of the counter does only need to account for the maximum difference of count values between the dark discharge phase of the photo diode and the longest illuminated discharge phase. So, if for example the maximum difference is 29 counts, then a five-bit counter (counts from zero to 31) is sufficient. The absolute maximum count values have no impact as long as the counter, when counting up, overflows from the largest positive value to the largest negative value and continues counting from there and, when counting down, underflows from the largest negative number immediately to the largest positive number and continues counting from there. This is the case for typical digital up-/down-counters.

The output signal of the detector apparatus can be used to perform any suitable control functions, to produce an alarm, wakeup signal or any other processing required.

All of the functions described above can be performed using alternative smoke detector configurations, examples of which are shown in FIG. 1b to 1d. These alternative configurations can have multiple emitter devices 12', as shown in FIG. 1b to 1d. The emitter devices 12' can include emitters generating light at different wavelengths, such as different color LEDs, and/or can be arranged so as to emit light at different angles, as shown in FIGS. 1b and 1d. The multiple emitter devices 12' would be connected to further outputs (OUTn, not shown) of the microprocessor or hardware controller. The described measurement procedures then can be performed in sequence for each of the emitter devices 12'. For example, a measurement sequence, as describe above and depending on the measurement circuit used, would first be performed by using a first emitter device; then it would be repeated using a second emitter device and so on. The use of multiple emitter devices 12' allows distinguishing between different kinds of smoke or other impurities in the air. This helps to prevent false alarms. For example, it would become easier to avoid that smoke from cooking, like water vapor or fat, would trigger an alarm and to ensure that only smoke from a fire will trigger the alarm. The present invention allows for a simple yet efficient extension of the measurement procedure and hardware from single-angle single-wavelength emitter devices to multi-color multi-angle emitter devices. The detector then can create multiple angle and color dependent measurement results which can be analyzed and qualified for dangerous conditions by suitable methods.

What is claimed is:

1. An apparatus comprising:
 a detector including a first input port, a second input port and a first output port, wherein at least the first output port is a tri-state port for selectively providing a high voltage output, a low voltage output and a high-impedance output;
 a sensor unit including an emitter device and a receiver device, the first output port coupled to the receiver device for charging and discharging a capacitance of the receiver device, the second input port coupled to the emitter device for driving the emitter device; and
 a microprocessor controlling a switch, the first output port and a second output port of the detector as a function of an output of an A/D converter circuit;
 wherein the microprocessor includes a control module, the control module generating a control sequence for a first measurement phase and a second measurement phase that:
 discharges the capacitance of the receiver device when the first and second output ports are at a low voltage;
 charges the capacitance of the receiver device when the first input port is at a high-impedance state and the first output port is at a high voltage;
 sets the first output port to a high-impedance state when an output voltage of the receiver device reaches a reference voltage;
 starts a timer, and after a first time period in the first measurement phase and after a second time period in the second measurement phase, charges and discharges the capacitance of the receiver device if the output voltage of the receiver device is equal to or smaller than the reference voltage, and if the output voltage is higher than the reference voltage respectively; in which the second output port is at the low voltage; and
 measures a first elapsed time $T_{2A}$ in the first measurement phase and measures a second elapsed time $T_{2B}$ in the second measurement phase, after the receiver device is at the reference voltage;
 in which the second measurement phase is after the first measurement phase in time and in which the control sequence, during an evaluation phase, derives the sensor output value from the second elapsed time $T_{2B}$ and the first elapsed time $T_{2A}$;
 wherein the detector includes the A/D converter circuit coupled to the receiver device via the first input port, to derive a sensor output value from the receiver device during a number of charging and discharging cycles.

2. The apparatus of claim 1, wherein the apparatus is implemented in an integrated circuit design.

3. The apparatus of claim 1, wherein the A/D converter circuit includes a comparator circuit and a timer, the comparator circuit coupled to the first input port for receiving an output of the receiver device and the timer coupled to an output of the comparator circuit, wherein the comparator circuit includes one of a Schmitt trigger and an operational amplifier.

4. The apparatus of claim 3, wherein the comparator circuit includes the Schmitt trigger.

5. The apparatus of claim 4, wherein the control module calculates a difference between the first elapsed time $T_{2B}$ and the second elapsed time $T_{2A}$ for deriving the sensor output value.

6. The apparatus of claim 5, wherein the control module calculates a duty cycle of $T_1/T_{2A}$ and a duty cycle of $T_1/T_{2B}$ for deriving a detector output value.

7. The apparatus of claim 1 further comprising the switch coupled between the first input port and a low voltage input, the detector controlling the switch and the first output port for charging and for discharging the capacitance of the receiver device.

8. The apparatus of claim 7 wherein the first elapsed time $T_{2A}$ is inverted if the output voltage of the receiver device is larger than the reference voltage, and wherein the second elapsed time $T_{2B}$ is inverted if the output voltage of the receiver device is larger than the reference voltage.

9. The apparatus of claim 1, wherein the A/D converter is a first A/D converter, wherein the second input port receives an operational parameter of the emitter device, and wherein the apparatus further comprises a second A/D converter circuit coupled to the second input port for deriving a digital operational value of the emitter device, wherein the detector uses the digital operational value of the emitter device for performing at least one of controlling the emitter device and adjusting the sensor output value.

10. The apparatus of claim 9, wherein the first and second A/D converter circuits are implemented by a same A/D converter circuit in combination with a multiplex circuit.

11. The apparatus of claim 1, further including a capacitor connected in parallel to the receiver device.

12. The apparatus of claim 1 wherein the sensor unit is an optical smoke detector, the emitter device is a light emitter, and the receiver device is one of a photo diode and a photo transistor.

13. A method comprising:
performing a sequence of charging and discharging cycles of a capacitance of a receiver device;
driving an emitter device selectively during the charging and discharging cycles;
measuring discharging times of the receiver device during the charging and discharging cycles; and
deriving an output signal from measured discharging times,
wherein measuring discharging times of the receiver device during the charging and discharging cycles comprises, in a first measurement phase and a second measurement phase:
discharging the capacitance of the receiver device when a first output port and a second output port are at a low voltage;
charging the capacitance of the receiver device when a first input port is at a high-impedance state and the first output port is at a high voltage;
setting the first output port to a high-impedance state when an output voltage of the receiver device reaches a reference voltage;
starting a timer, and after a first time period in the first measurement phase and after a second time period in the second measurement phase, charging and discharging the capacitance of the receiver device if the output voltage of the receiver device is equal to or smaller than the reference voltage, and if the output voltage is higher than the reference voltage respectively; in which the second output port is at low voltage; and
measuring a first elapsed time $T_{2A}$ in the first measurement phase and measuring a second elapsed time $T_{2B}$ in the second measurement phase, after the receiver device is at reference voltage;
in which the second measurement phase is after the first measurement phase in time and in which the control sequence during an evaluation phase derives a sensor output value from the second elapsed time $T_{2B}$ and the first elapsed time $T_{2A}$.

14. The method of claim 13 wherein performing, driving, measuring and deriving are performed via a processing device.

15. The method of claim 14 wherein the processing device includes a Schmitt trigger circuit and a timer, wherein the Schmitt trigger circuit in combination with the capacitance of the receiver is part of an A/D converter for deriving the sensor output value.

16. The method of claim 13 further comprising calculating and a duty cycle of $T_1/T_{2A}$ and a duty cycle of $T_1/T_{2B}$ for deriving the sensor output value.

17. The method of claim 13 wherein the emitter device is a light emitter, and the receiver device is a light receiver.

* * * * *